(12) United States Patent
Abelyan et al.

(10) Patent No.: US 7,838,044 B2
(45) Date of Patent: Nov. 23, 2010

(54) **EXTRACTION, SEPARATION AND MODIFICATION OF SWEET GLYCOSIDES FROM THE *STEVIA REBAUDIANA* PLANT**

(75) Inventors: Varuzhan H. Abelyan, Negeri Sembilan (MY); Vahe T. Ghochikyan, Negeri Sembilan (MY); Avetik A. Markosyan, Negeri Sembilan (MY); Mariam O. Adamyan, Negeri Sembilan (MY); Lidia A. Abelyan, Negeri Sembilan (MY)

(73) Assignee: PureCircle Sdn Bhd, Negeri Sembilan (MY)

( * ) Notice: Subject to any disclaimer, the term of this patent is extended or adjusted under 35 U.S.C. 154(b) by 104 days.

(21) Appl. No.: 11/016,781

(22) Filed: Dec. 21, 2004

(65) Prior Publication Data

US 2006/0134292 A1 Jun. 22, 2006

(51) Int. Cl.
*A61K 36/00* (2006.01)
(52) U.S. Cl. .................................................. 424/725
(58) Field of Classification Search ................ None
See application file for complete search history.

(56) References Cited

U.S. PATENT DOCUMENTS

| | | | |
|---|---|---|---|
| 4,082,858 A | | 4/1978 | Morita et al. |
| 4,219,571 A | | 8/1980 | Miyake |
| 4,361,697 A | | 11/1982 | Dobberstein et al. |
| 4,590,160 A | * | 5/1986 | Nishihashi et al. ............ 435/78 |
| 4,892,938 A | | 1/1990 | Giovanetto |
| 5,070,081 A | * | 12/1991 | Majid et al. .................... 514/58 |
| 5,433,965 A | * | 7/1995 | Fischer et al. ................ 426/548 |
| 5,962,678 A | | 10/1999 | Payzant et al. |
| 5,972,120 A | | 10/1999 | Kutowy et al. |

FOREIGN PATENT DOCUMENTS

| JP | 57086264 A | * | 5/1982 |
|---|---|---|---|
| JP | 11243906 A | * | 9/1999 |

OTHER PUBLICATIONS

1989. Phillips et al. Development in Sweeteners- vol. 3. pp. 1-39.*
Translation of JP 57086264 A (listed above). Document No. Sho 57 [1982]-86264.*
Abelian et al. Characteristics of Cyclodextrin Production Using Cyclodextrin Glucanotransferases of Various Groups of Microorganisms. Prikl Biokhim Mikrobiol. 2002. Nov.-Dec. 38. (6) Abstract.*
Abelyan et al. Characteristics of Cyclodextrin Production Using Cyclodextrin Glucanotransferases From Various Groups of Microorganisms. Applied Biochemistry and Microbiology, vol. 38, No. 6, 2002. pp. 527-535. Translated from Prikladnaya Biokhimiya i Mikrobiologiyya, vol. 38, No. 6 2002. pp. 616-624.*
Chang, S. S. et al., "Stability studies of stevioside and rebaudioside A in Carbonated beverages," J. Agric. Food Chem., vol. 31, 1983, pp. 409-412.
DuBois, G. E. et al., "Diterpenoid sweeteners. Synthesis and sensory evaluation of stevioside analogues with improved organoleptic properties," J. Med. Chem, vol. 28, 1984, pp. 93-98.
Kitahata, S. et al., "Production of rubusoside derivatives by transglycosylation of various beta-galactosidase," Agricultural and Biological Chemistry, vol. 53, 1989, pp. 2923-2928.
Lobov, S.V. et al., "Enzymatic production of sweet stevioside derivatives: transglycosylation by glucosidases," Agricultural and Biological Chemistry, vol. 55, 1991, pp. 2959-2965.
Tanaka, O., "Improvement of taste of natural sweetners," Pure Appl. Chem, vol. 69, 1987, pp. 675-683.
Phillips, K. C., "Stevia: steps in developing a new sweetener," from "Developments in sweeteners," T.H. Grenby, Editor, vol. 3, 1989, Elsivier Applied Science, London, pp. 1-43.
Schiffman, S. S. et al., "Investigation of synergism in binary mixtures of sweeteners," Brain Res. Bull, vol. 38, 1995, pp. 105-120.
Yamamoto, K. et al., "Effective production of glucosyl-stevioside by alpha-1, 6-transglucosylation of dextran dextranase," Bioscience, Biotechnology, and Biochemistry, vol. 58, 1994, pp. 1657-1661.

* cited by examiner

*Primary Examiner*—Christopher R Tate
*Assistant Examiner*—Melenie McCormick
(74) *Attorney, Agent, or Firm*—Pyprus Pte Ltd

(57) ABSTRACT

The invention disclosed relates to a method for the extraction of sweet glycosides from the *Stevia rebaudiana* Bertoni plant and recovery of individual rebaudioside A and stevioside. The extraction is developed in the presence of pectinase, and the extract is purified using cyclodextrin and bentonite. High purity rebaudioside A is obtained by crystallization and recrystallization from ethanol. High purity stevioside is prepared from the filtrate by purification with cyclodextrin, bentonit, and ion exchange resins. The enzymatic modification of the rebaudioside A, stevioside and the purified extract is carried out using the transferring enzymes derived from *Thermoactinomyces vulgaris* and *Bacillus halophilus*.

10 Claims, 11 Drawing Sheets

EXTRACTION, SEPARATION AND MODIFICATION OF SWEET GLYCOSIDES FROM THE *STEVIA REBAUDIANA* PLANT

FIELD OF THE INVENTION

The invention relates to a method for the extraction of sweet glycosides from the *Stevia rebaudiana* Bertoni plant and recovery of individual rebaudioside A and stevioside.

The present invention also relates to a novel transferring enzymes capable of catalyzing the efficient transglucosylation of stevioside, rebaudioside A and the mixture of glycosides.

BACKGROUND OF THE INVENTION

The worldwide demand for high potency sweeteners is increasing and, with blending of different sweeteners becoming a standard practice, the demand for alternatives is expected to increase. The sweet herb of Paraguay, *Stevia rebaudiana* Bertoni, produces an alternative sweetener with the added advantage that *Stevia* sweeteners are natural plant products. In addition, the sweet steviol glycosides have functional and sensory properties superior to those of many high potency sweeteners.

The sweet diterpene glycosides of *Stevia* have been characterized and eight sweet glycosides of steviol have been identified. These glycosides accumulate in *Stevia* leaves where they may comprise from 10 to 20% of the leaves dry weight. On a dry weight basis, a typical profile for the four major glycosides found in the leaves of *Stevia* comprises 0.3% dulcoside, 0.6% rebaudioside C, 3.8% rebaudioside A and 9.1% stevioside. Other glycosides identified within *Stevia* include rebaudioside B, C, and E, and dulcosides A and B. Rebaudioside B may be an artifact formed from rebaudioside A during extraction since both rebaudioside A and rebaudioside D are found to convert to rebaudioside B by alkaline hydrolysis.

Of the four major diterpene glycoside sweeteners present in *Stevia* leaves only two, stevioside and rebaudioside A, have had their physical and sensory properties well characterized. Stevioside and rebaudioside A were tested for stability in carbonated beverages and found to be both heat and pH stable (Chang and Cook, 1983). Stevioside is between 110 and 270 times sweeter than sucrose, rebaudioside A between 150 and 320 times sweeter than sucrose, and rebaudioside C between 40 and 60 times sweeter than sucrose. Dulcoside A was 30 times sweeter than sucrose. Rebaudioside A was the least astringent, the least bitter, had the least persistent aftertaste and was judged to have the most favorable sensory attributes of the four major steviol glycosides (Phillips, 1989 and Tanaka, 1997). Dubois and Stephanson (1984) have also confirmed that rebaudioside A is less bitter than stevioside and demonstrated that the bitter notes in stevioside and rebaudioside A are an inherent property of the compounds and not necessarily the result of impurities in whole plant extracts. Bitterness tends to increase with concentration for both stevioside and rebaudioside A. Both stevioside and rebaudioside A are synergistic in mixtures with other high potency sweeteners such as aspartame and are good candidates for inclusion in blends (Schiffman et al. 1995).

A process for the recovery of diterpene glycosides, including stevioside from the *Stevia rebaudiana* plant is described (U.S. Pat. No. 4,361,697). A variety of solvents, having different polarities, were used in a sequential treatment that concluded with a high performance liquid chromatographic (HPLC) separation procedure.

The method for the recovery of rebaudside A from the leaves of *Stevia rebaudiana* plants is developed (U.S. Pat. No. 4,082,858). Again, final purification is achieved by liquid chromatography subsequent followed by an initial extraction with water an alkanol having from 1 to 3 carbon carbons, preferably methanol. It is also disclosed that water may be used as the initial solvent, their preferred solvent at this stage is a liquid haloalkane having from 1 to 4 carbon atoms. The preferred second solvent is an alkanol having from 1 to 3 carbon atoms, while the preferred third solvent is an alkanol having from 1 to 4 carbon atoms and optionally minor amounts of water.

U.S. Pat. No. 4,892,938, to Giovanetto discloses a purification process in which the aqueous extracts of the plant are purified by passing these aqueous extracts through a series of ion-exchange resins which are selected to remove various impurities. The sweet glycosides remain in the water and are recovered by evaporation of the water. The advantage is that everything is done in water, while most other processes involve the use of a solvent at some point. The disadvantage is that the final product is quite impure with only about 70% is a mixture of the sweet glycosides. The balance is mainly material more polar than the sweet glycosides which we have identified as a complex mixture of polysaccharides (about 25%), and a small amount of yellow, oily material less polar than the sweet glycosides (about 5%).

The low polarity oil was isolated by chromatography. The flavor of the low polarity oil is very unpleasant. We have found this oil to be present in varying levels from 0.2 to 2.0% in every commercial product we have examined. Since of varying amounts this intensely off-flavored material is contained in the commercial materials it presents problems with quality control and flavor issues. The polysaccharide fraction also appears to contain off-flavor materials, but not as intense in flavor as the low polarity yellow oil.

The sweet glycosides obtained from Giovanetto process are always a mixture. We have determined that the two principle sweet glycosides are Stevioside and Rebaudioside A, and two of the minor sweet glycosides are Dulcoside and Rebaudioside C, although there are many other minor ones. We have isolated the two principle glycosides and we have found that there is a considerably different flavor between them with one being much more desirable than the other. Stevioside has an aftertaste which is undesirable. This aftertaste is present in Stevioside samples of even greater than 99% purity. On the other hand, Rebaudioside A does not possess an aftertaste and has a sweetness flavor comparable to sucrose. Thus it is recognized as having the most desirable sensory properties. In addition to this complexity, various impurities are also present and some of these possess undesirable flavors. The entire matter is further clouded by the extreme difficulty of doing analyzes. The analytical exercise pushes at the envelope of present technology and involves considerable art. Finally, the problem with the methods described above is that the resulting materials contain a mixture of all of the sweet glycosides.

The combined use of microfiltration, ultrafiltration, and nanofiltration is also applied for the purification of *stevia* extract (U.S. Pat. No. 5,972,120). The method gives a good result, however the application of the above mentioned equipments makes the product cost very expensive. Besides, the process again provided to isolate only the mixture of glycosides, but not pure individual compounds, such as stevioside and rebaudioside A.

Individual sweet glycosides are obtained from the *stevia rebaudiana* plant. A mixture of sweet glycosides extracted from the *stevia rebaudiana* plant is processed to remove impurities by using two ion exchange columns. After removing the mixed sweet glycosides from the second column with methanol the solution is dried. Upon refluxing the dried solids in a methanol solution and then cooling the solution, Stevioside precipitates out. The filtrate is further concentrated and cooled to precipitate out Rebaudioside A. This Rebaudioside A can be further purified as can the previously obtained Stevioside (U.S. Pat. No. 5,962,678). However, a large amount of toxic organic solvent, such as methanol is used.

However, stevioside possesses residual bitterness and aftertaste, which affect its qualitative characteristics. They can be eliminated by the reaction of intermolecular transglycosylation of various enzymes, upon which the attachment of new carbohydrates at positions C13 and C19 takes place. It is the number of carbohydrate units in the above-mentioned positions that determines the quality and degree of component's sweetness.

Pullulanase, isomaltase (Lobov et al., 1991), β-galactosidase (Kitahate et al., 1989), and dextrine saccharase (Yamamoto et al., 1994) are used as transglycosylating enzymes, with pullulan, maltose, lactose, and partially hydrolyzed starch, respectively, being as donors.

The treatment with pullulanase results in production of 13-O-[β-maltotriosyl-(1,2)-β-D-glucosyl]-19-O-β-D-glucosyl-steviol; 13-O-[β-maltosyl-(1,2)-β-D-glucosyl]-19-O-β-D-glucosyl-steviol and 13-O-[β-sephorosyl-19-O-β-maltotriosyl-steviol. Although the yields of the transglycosylated products were rather low, the selectivity in terms of the yield of the desirable mono- and di-derivatives was higher than in the case of CGTase (Lobov et al., 1991).

In case of maltase, three transglycosylated products are also produced, namely 13-O-[β-sephorosyl-19-O-β-isomaltosyl-steviol; 13-O-[β-isomaltosyl-(1,2)-β-D-glucosyl]-19-O-β-D-glucosyl-steviol and 13-O-[β-nigerosyl-(1,2)-β-D-glucosyl]-19-O-β-D-glucosyl-steviol.

The transglucosylation of stevioside was also done by action of cyclodextrin glucanotransferases (CGTase) produced by *Bacillus stearothermophilus* FERM-P No 2222 (U.S. Pat. No. 4,219,571). However, the commercialized stevioside consisting of roughly equal amounts of purified stevioside and lactose was used as substrate, and the transferring reaction is not investigated on pure stevioside, pure rebaudioside A, and purified *stevia* mixture.

The object of the present invention is to provide an advantageous process for the extraction of sweet glycosides from *Stevia rebaudiana* Bertoni plant, and for the isolation of stevioside and rebaudioside A, and a second object of the present invention is to provide a novel transferring enzyme produced by *Themoactinomyces vulgaris* and *Bacillus halophilus* which catalyzes the transglucosylation of stevioside and rebaudioside A, as well as the mixture of the glycosides obtained after extraction.

SUMMARY OF INVENTION

The present invention relates to a method of increasing the rate of extraction for the recovering diterpene glycosides from *Stevia rebaudiana* plant, separation of stevioside and rebaudioside A, and their enzymatic modification. The invention seeks to simplify the processes.

In accordance with the present invention, a process for recovering sweet glycosides from the *Stevia rebaudiana* plant material is provided. The dried and powdered leaves are treated with water in the presence of a pectinase, cellulase, and α-amylase. The use of such enzymes considerably increased the extraction rate and facilitates the next stages of purification. The resulted extract is purified using treatment with calcium hydroxide and ultrafiltration. The permeate is passed through the column packed with bentonite and concentrated to syrup state under vacuum. The treatment with ethanol allows separating the practically pure rebaudioside A from the mixture. The rebaudioside A with high purity is obtained after washing the crystals with 88-95% of ethanol.

From the remaining solution stevioside is isolated after evaporation of ethanol, deionization by ion exchange resins, treatment with bentonite and spray drying. The high purity stevioside is obtained after washing the crystals with 97-98% of ethanol.

For the producing the mixture of sweet glycosides the treatment with ion exchangers and bentonite is carried out without isolation of rebaudioside A.

The application of cyclodextrin glucanotransferases of *Thermoactinomyces vulgaris* and *Bacillus halophilus* with high transferring activity allows increasing of the degree of transglycosylation of stevioside and decreasing of the time of the reaction.

DETAILED DESCRIPTION OF THE INVENTION

Diterpene glycosides, including sweet-testing substances, are found in the stems, seeds and leaves of the *S. rebaudiana* plant, being present in the highest concentration in the leaves. The leaves, therefore, are the preferred starting material for recovery of sweet glycosides. It is preferred that plant material be air dried before extraction, preferably at the temperatures between 50-60.degree.C. for a period 2-3 hours to a moisture content of 5-8%. Under these conditions the sweet glycosides are not decomposed. It has been found that the smaller the size of leaves the higher the rate of extraction. Mesh sizes of 20-30 (U.S. Sieve Series) are preferred. The proportion of extraction water preferably is about 5 liters to about 15 liters (pH 6.0 to 7.0) to one kilogram of leaves. Higher volumes of solvent can be used however it is not preferable from the practical standpoint. The duration of extraction may be from 0.5 hours to 24 hours, with a period of from about 1 hour to about 6 hours preferred.

The extraction temperature can be in the limits of 25-90.degree.C., however the temperatures between 45-75.degree.C. are more preferable.

The filtration rate and the clarification of extracts are enhanced when extraction is done in the presence of commercial pectinase (made by NOVOZYMES under the trade name of PECTINEX Ultra-SP-L) in the amount between 1-4 grams per one liter, preferably about 2 grams.

The plant material is separated from the solution by filtration and the pH of the filtrate is adjusted to about 10 with calcium hydroxide and heated between 40-60.degree.C., preferably from 50.degree.C. to 55.degree.C., for about 0.5-1.5 hours, cooled to ambient temperature with slow agitation, and finally filtered.

The pH of resulted filtrate is adjusted between 6.5-7.0 with any of mineral or organic acids, preferably phosphoric acid, and beta cyclodextrin is added in the amount 1-5%, preferably 2.0-2.5%, heated to 50-55.degree.C. for about 1-2 hours with agitation. Then, the solution is cooled to the 10-12.degree.C. for about 1 hours. The formed precipitate is removed by filtration.

The almost clear solution is mixed with bentonite for water based systems (Sigma-Aldrich) in the amount 1-5 grams per liter, preferably about 2-3 grams, and mixed at 40-45.degree.C. for about one hour. The remaining clear solution is drawn off, filtered, and thickened at 50-55.degree.C., in vacuum to a syrup state.

Figure 1:
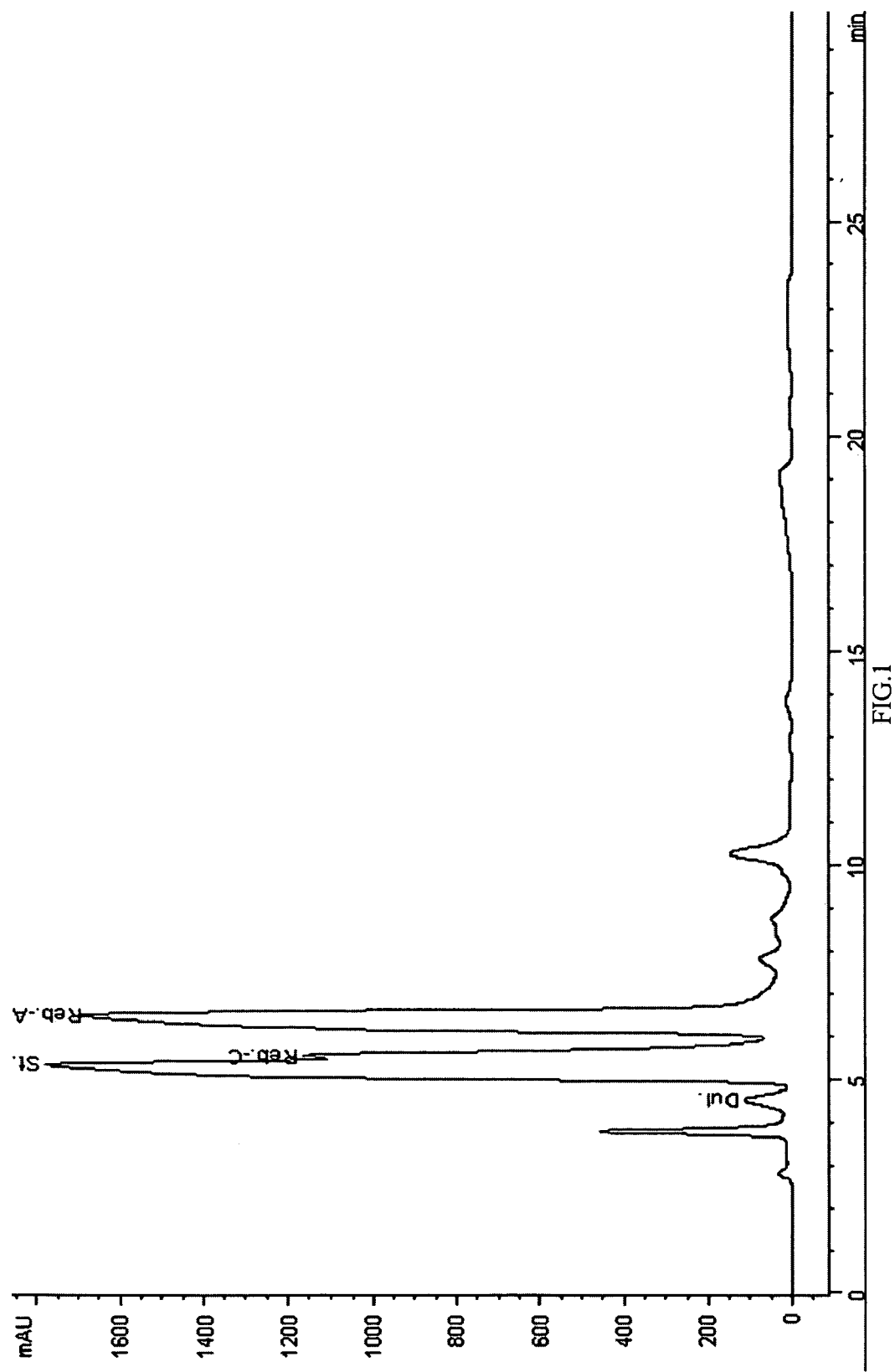
FIG. 1 shows a high-performance liquid chromatographic chart of purified extract.

The HPLC analysis data of the obtained product, carried out at Agilent Technologies 1100 Series (USA) equipped with Zorbax-NH$_2$ column using acetonitrile-water gradient from 80:20, v/v (2 minutes) to 50:50, v/v during 70 minutes, or acetonitrile-water=70/30, v/v without any gradient and UV detector at 210 nm is presented in the FIG. 1.

Figure 2:
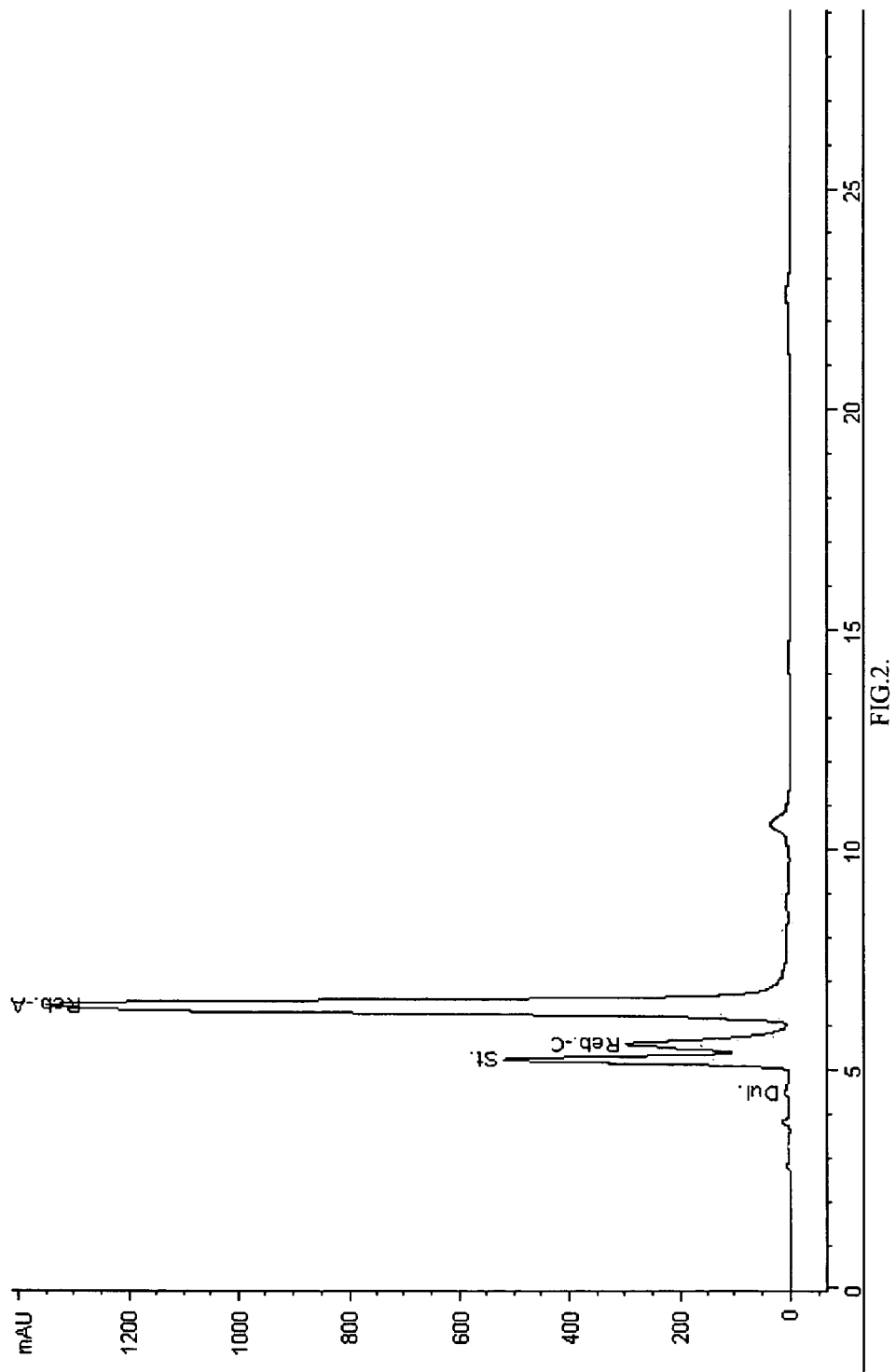
FIG. 2 shows a high-performance liquid chromatographic chart of rebaudioside A after the first crystallization.
Figure 3:
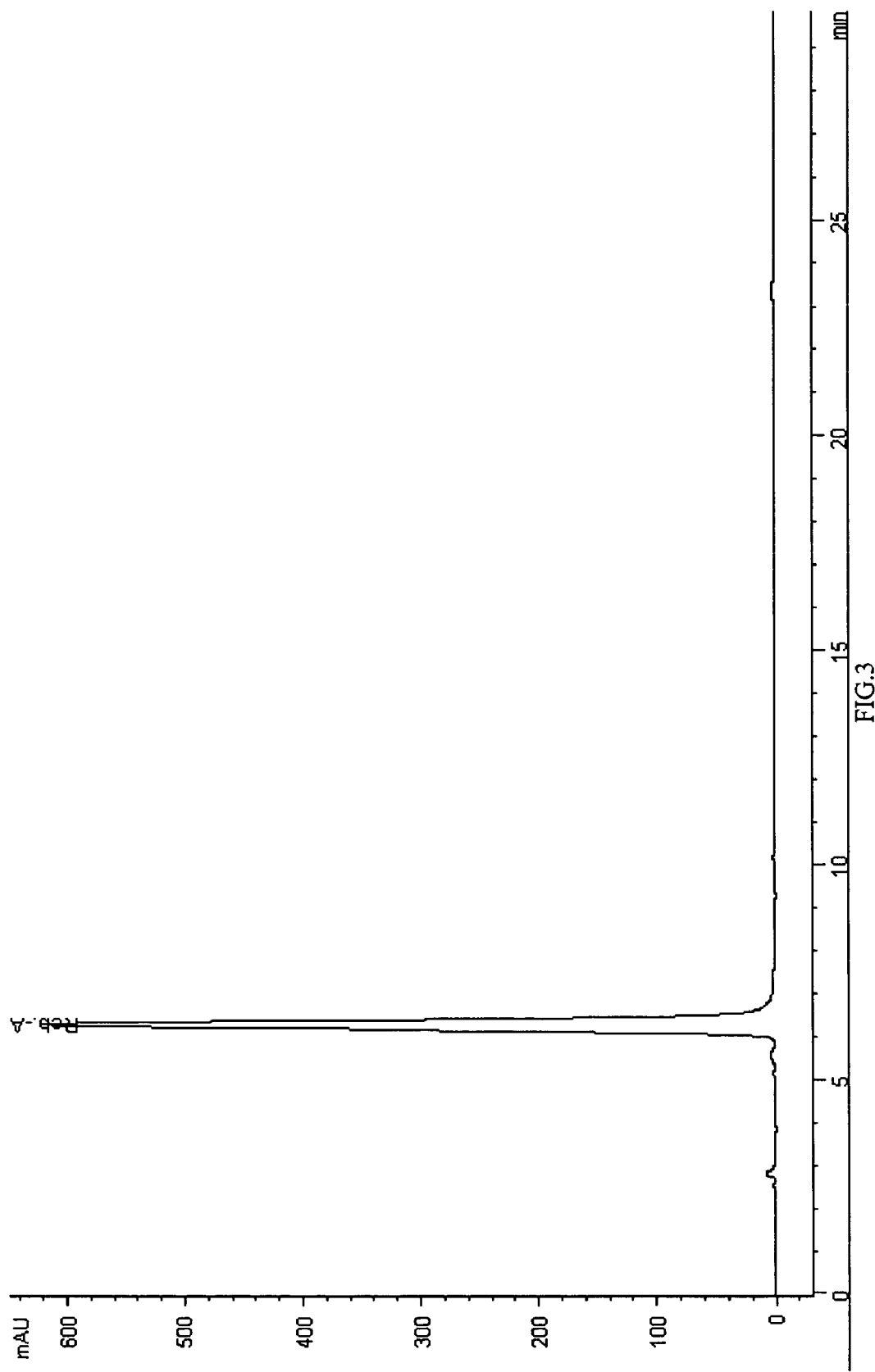
FIG. 3 shows a high-performance liquid chromatographic chart of rebaudioside A after recrystallization.

The obtained syrup is mixed with 96.2% of ethanol and maintain at 45-50.degree.C. for 30 minutes with agitation. The proportion of syrup and ethanol is between 1:2-1:7, w/v, preferably 1:5. During this time the precipitate is formed, which is filtered and dried. According to the HPLC analysis the powder contents around 83-84% of rebaudioside A (FIG. 2). For the further purification the powder is mixed with five volumes of 95% of ethanol, and treated as in the case of syrup. The rebaudioside A with 98.5% of purity is obtained (FIG. 3).

Figure 4:
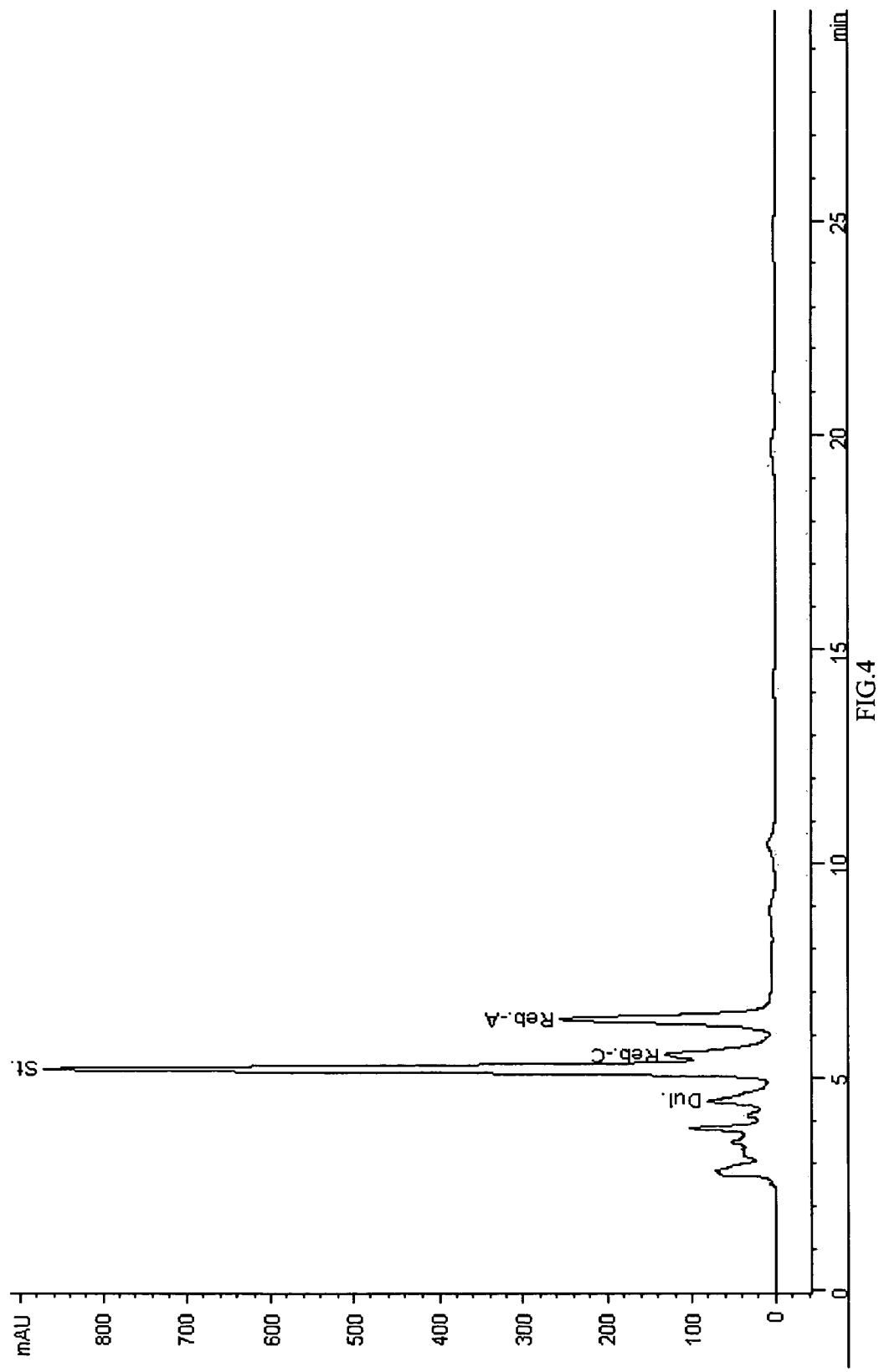
FIG. 4 shows a high-performance liquid chromatographic chart of remaining solution after precipitation of rebaudioside A.

The liquid filtrate is used for the next step to recover the stevioside (FIG. 4).

Figure 5:
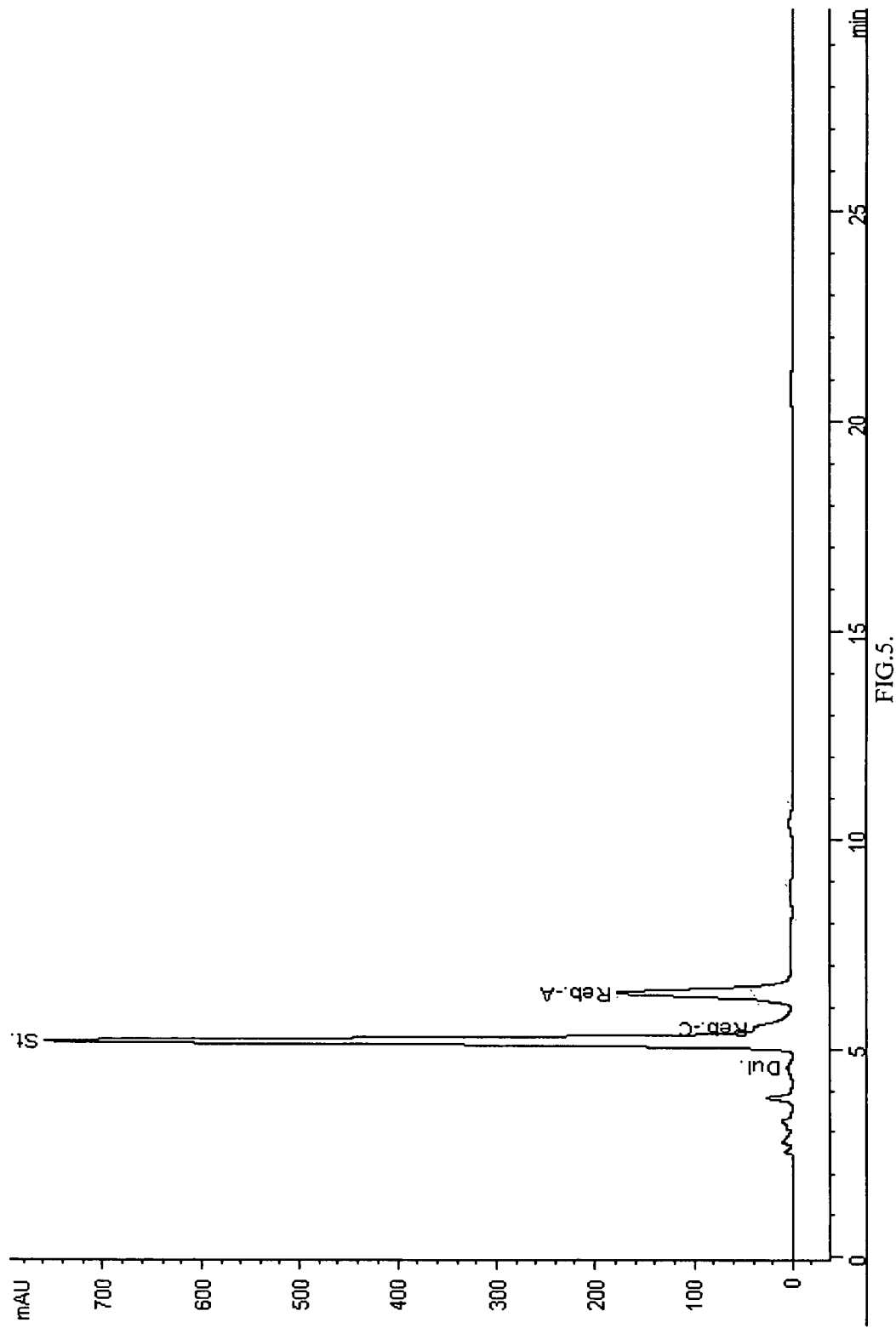
FIG. 5 shows a high-performance liquid chromatographic chart of stevioside after the first crystallization.
Figure 6:
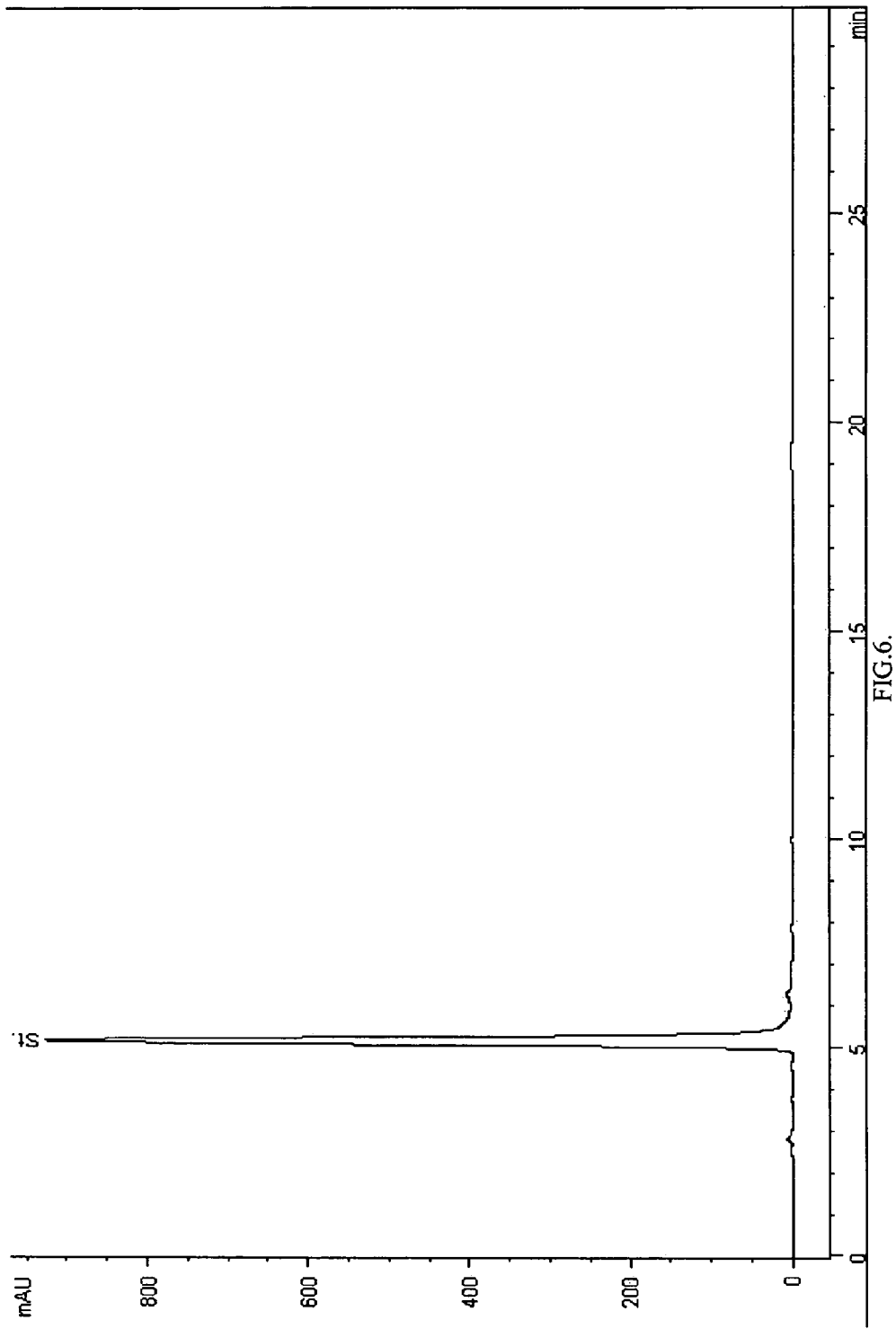
FIG. 6 shows a high-performance liquid chromatographic chart of stevioside after recrystallization.
Figure 7:
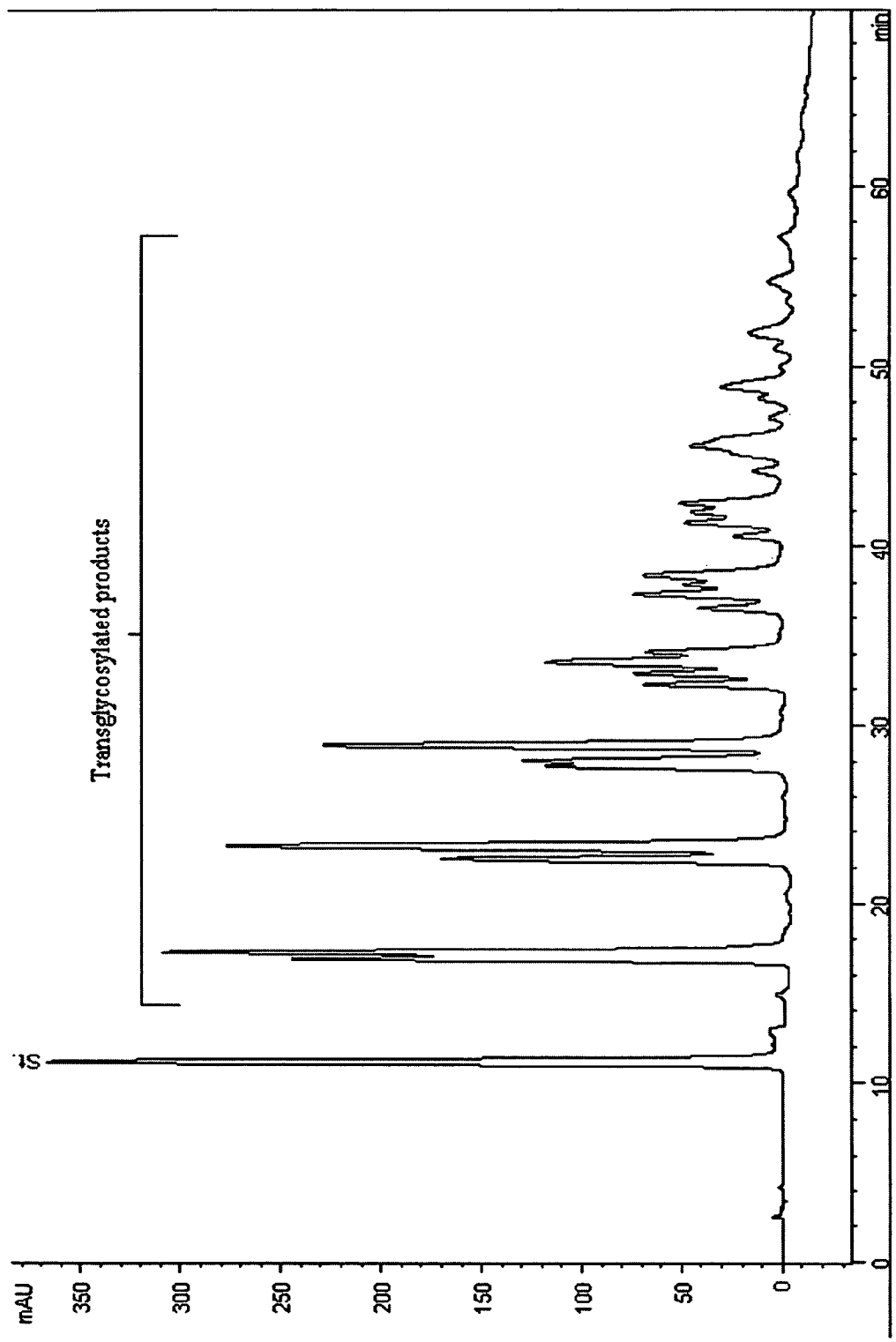
FIG. 7 shows a high-performance liquid chromatographic chart of a CGTase-treated stevioside.
Figure 8:
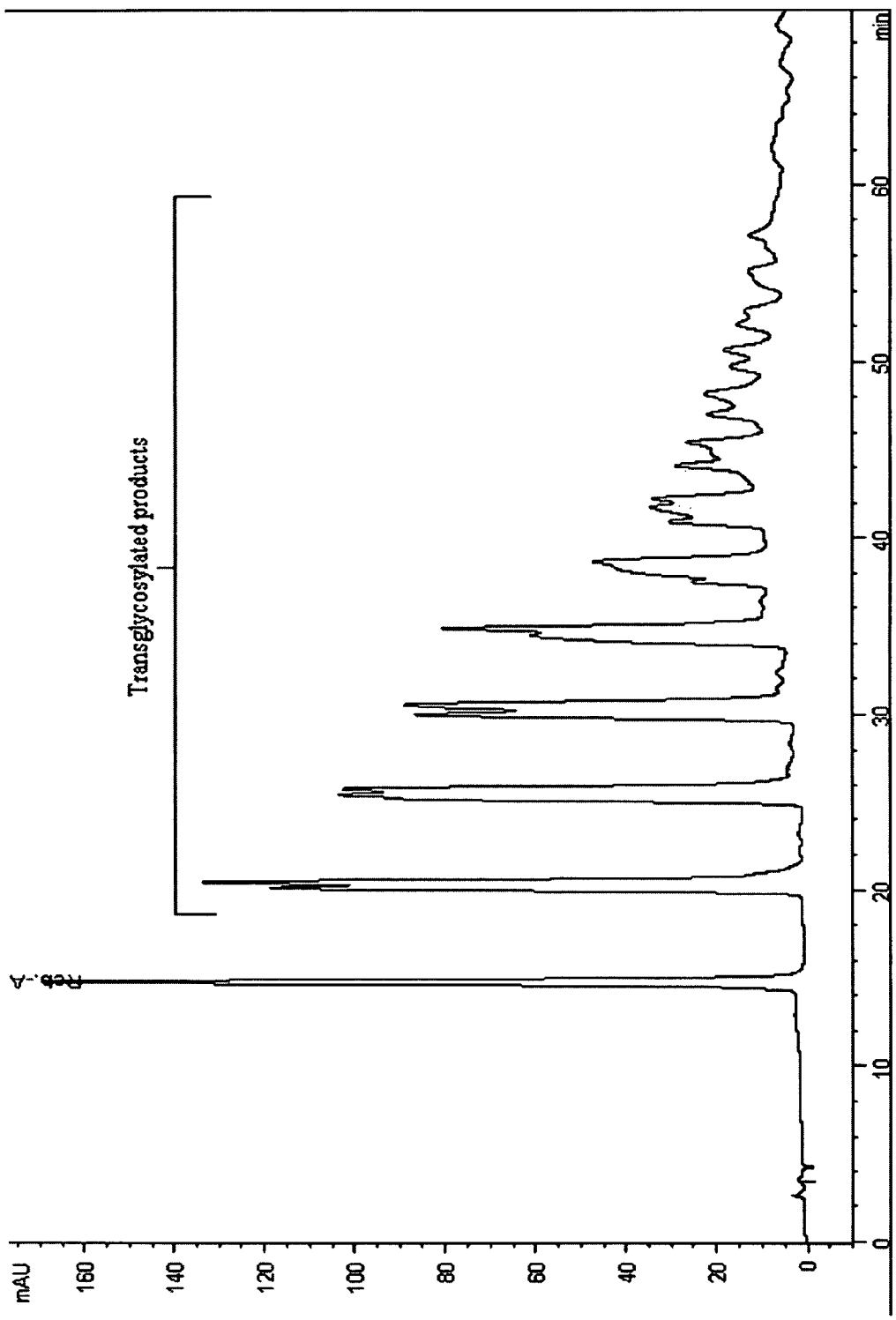
FIG. 8 shows a high-performance liquid chromatographic chart of a CGTase-treated rebaudioside A.
Figure 9:
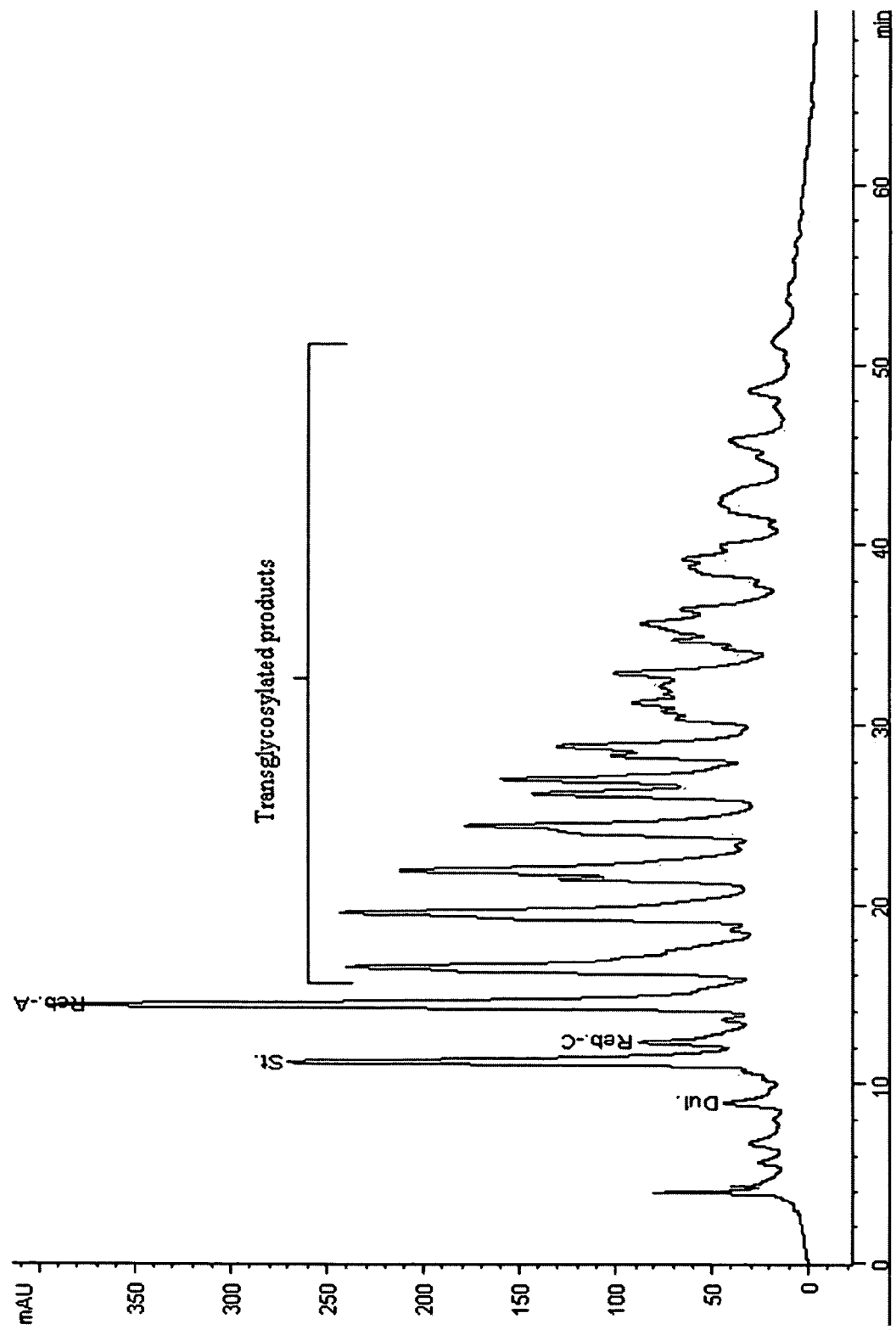
FIG. 9 shows a high-performance liquid chromatographic chart of a CGTase-treated purified extract.

The filtrate is mixed with bentonite for organic systems (Sigma-Aldrich) in the amount 1-5 grams per liter, preferably about 2-3 grams, and mixed at 40-45.degree.C. for about one hour. The suspension is filtered, mixed with equal volume of distilled water, and the ethanol is removed by vacuum evaporation. Deionization of the resulted solution is developed by conventional methods using ion exchange resins, such as Dowex 50WX4-200 (H type) and Amberlite IRA96 (OH type), concentrated and dried. The resulted powdered stevioside have about 93% of purity (FIG. 5). For the further purification the powder is mixed with two volumes of 90% of ethanol, and at 10-12.degree.C. maintained for about 30 minutes with slow agitation. The precipitate is separated by filtration and dried under vacuum. The stevioside with about 98.0-98.5% of purity is obtained (FIG. 6).

For the production of the purified *stevia* extract only without separation of individual compounds the solution after removing the leaves and treatment by calcium hydroxide, cyclodextrin, and bentonite is deionized, concentrated and dried.

The enzymatic transglycosylation of sweeteners obtained is developed with CGTases produced by cultures *Thermoactinomyces vulgaris* INMIA (Institute of microbiology of the National Academy of Sciences of Armenia)-Tac-3554 and *Bacillus halophilus* BIO-12H. CGTase producers have been identified among thermoactinomycets and halophilic bacilli for the first time.

The colonies of *T. vulgaris* fast growing, flat at 50.degree.C., with moderate covering of white mycelium and a feathery margin on used nutrient medium. The colony reverse is white. No soluble pigments are produced.

Substrate mycelium well-developed, branched, septate, 0.6-0.75 μm in diameter. Aerial mycelium 0.7-0.9 μm diameter. Spores formed singly on aerial and substrate hyphae, spheroidal, 0.53-1.0 μm in diameter.

The colonies of *B. halophilus* on the nutrient agar medium at 37.degree.C. are round with entire margins, cream-colored, flat, not-brilliant.

Figure 10:
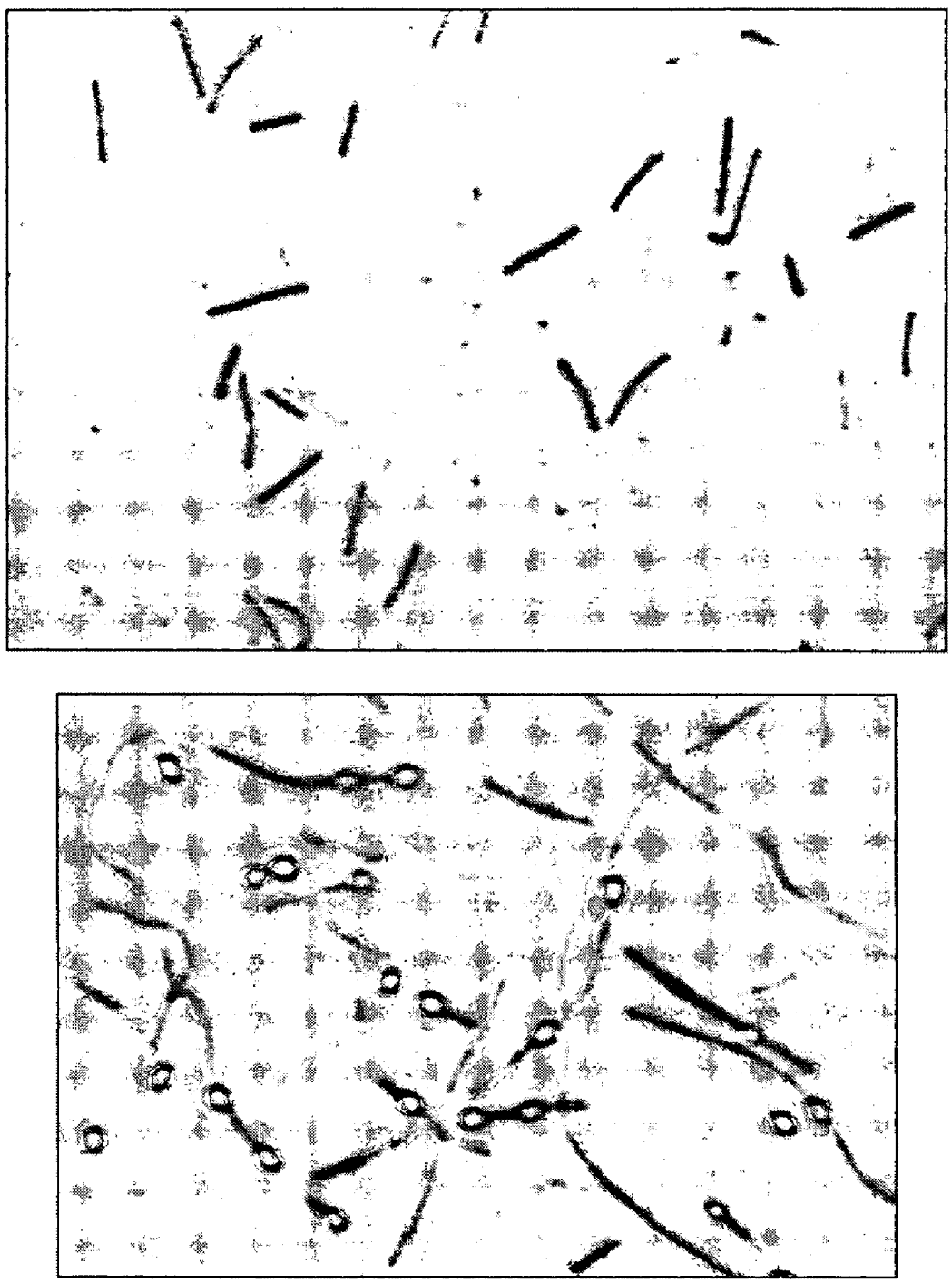
FIG. 10 shows the morphological characteristics of *Bacillus halophilus* BIO-12H. (a) is vegetative cells; (b)—sporulated cells and spores, ×1000.
Figure 11:
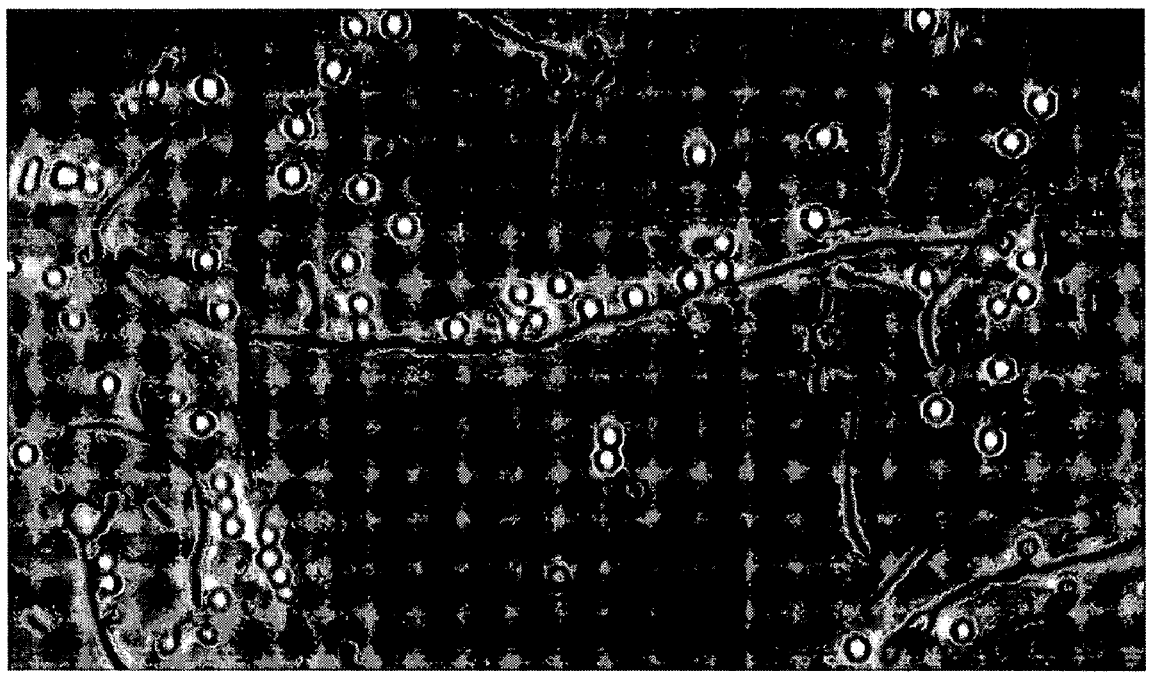
FIG. 11 shows the morphological characteristics of *Thermoactinomyces vulgaris* INMIA-Tac-3554.

The morphological and physiological characteristics of the strains are presented in the TABLE 1, FIG. 10 and FIG. 11.

TABLE 1

| Properties | Characteristics | |
|---|---|---|
| | T. vulgaris | B. halophilus |
| Cells size | – | Rod-shaped, 0.4-0.83 × 2.0-4.3 μm, gram-positive, motile |
| Spore size | 0.53-1.0 μm | 0.7-0.9 μm |
| Spores form | S | S |
| Spore position | – | T |
| Sporangium swollen | – | + |
| Catalase | + | + |
| Formation of dihydroxiacetone | + | + |
| V-P reaction | – | + |
| Reaction on lecithinase | ND | + |
| Nitrate reduction | + | – |
| Hydrolysis of starch | + | + |
| Hydrolysis of hippurate | – | – |
| Utilization of citrate | + | – |
| Hydrolysis of casein | + | – |
| Hydrolysis of gelatin | + | – |
| Acid from arabinose, xylose, mannitol, glucose, galactose, lactose, cyclodextrins, maltotriose, mannose, salicin, fructose | +/–gas | +/–gas |
| Growth at pH 5.7 | + | + |
| Growth at 65. degree. C. | + | – |
| Growth at 50. degree. C. | + | + |
| Anaerobic growth | – | + |
| Deamination of Phe | – | – |
| Growth in presence of NaCl | | |
| 5% | – | + |
| 7% | – | + |
| 10% | – | + |
| more than 15% | – | + |
| Formation of urease | – | – |
| Formation of indole | – | – |
| Formation of hydrogen sulphide | – | – |
| Degradation of tyrosine | + | – |

The cultivation of *T. vulgaris* usable in the present invention is conducted under aerobic conditions at a temperature of, usually, 45-60.degree.C., preferably, 49-55.degree.C.; and a pH of 5-8, preferably, 6.8-7.2. The cultivation time is 20-22 hours. The aeration rate is adjusted in the range of 0.5:1.0 v/v per one minute, preferably, 1:1.

The cultivation of *B. halophilus* is conducted under aerobic conditions at a temperature of, usually, 27-40.degree.C., preferably, 30-37.degree.C.; and a pH of 5-8, preferably, 6.8-7.2.

The cultivation time is 24-36 hours. The aeration rate is adjusted in the range of 0.5:1.0 v/v per one minute, preferably, 1:1.

The cultivation is carried out in a batch-wise or a continuous manner.

Any synthetic and natural nutrient culture media can be used for the cultivation of the microorganisms. Any carbon-containing substances can be used in the invention as carbon sources. For instance, saccharides such as sucrose, maltose, dextrin, glucose, lactose, galactose, cyclodextrins, and starch, as well as saccharide-containing products such as molasses and yeast extracts, can be used as the carbon sources. The concentrations of these carbon sources in nutrient culture media are selectively chosen depending on their types. However, the best results for both of microorganisms are obtained in the case of 0.7-2.0% of starch, preferably, 0.9-1.2%. The nitrogen sources usable in the present invention are, for example, inorganic nitrogen-containing compounds such as ammonium salts; and organic nitrogen-containing compounds such as urea, corn steep liquor, casein, peptone, yeast extract, and beef extract. The inorganic ingredients usable in the present invention are, for example, calcium salts, magnesium salts, potassium salts, sodium salts, phosphates and others.

Since the CGTase activity is found in the cell-free nutrient media, the media can be collected and used as a crude enzyme. Conventional liquid-solid separation methods can be used to remove cells. For example, methods to directly centrifuge the culture and those to filtrate with pre-coat filters or to separate cells by membrane filtration using plain filters or hollow-fibers. The resulting cell-free culture broth can be used intact as a crude enzyme, and preferably, used after concentration. The concentration methods usable in the present invention are, for example, salting out using ammonium sulfate, sedimentation using acetone and/or alcohol, and concentration using ultrafiltration membranes such as plain filters and hollow-fibers.

Crude enzymes can be immobilized by conventional methods such as adsorption, covalent biding, and entrapping.

Crude enzymes can be used intact and after purification. For example, cell-free culture broth is concentrated using ultrafiltration membranes, and purified successively on beta cyclodextrin polymers to obtain an enzyme preparation exhibiting an electrophoretically single protein band.

Some properties of the CGTases are presented in TABLE 2.

TABLE 2

| Microbial strains | Mol. weight, kDa | Optimum pH | pH-stability | Thermal stability, degree. C. | Cyclodextrin produced |
|---|---|---|---|---|---|
| B. halophilus | 70 | 6.5-7.0 | 6.0-9.0 | 50 | β >> γ |
| T. vulgaris | 64 | 6.0-7.0 | 5.5-8.5 | 70 | β > α > γ |

The amino acid composition of the enzymes is presented in the TABLE 3.

TABLE 3

| Amino acides | Number of residues, % | |
|---|---|---|
| | T. vulgaris | B. halophilus |
| Asp + Asn | 18.3 | 17.4 |
| Thr | 8.7 | 9.1 |
| Ser | 6.3 | 7.5 |
| Glu + Gln | 8.2 | 5.5 |
| Pro | 5.0 | 4.5 |

TABLE 3-continued

| Amino acides | Number of residues, % | |
|---|---|---|
| | T. vulgaris | B. halophilus |
| Gly | 9.5 | 9.8 |
| Ala | 8.0 | 9.4 |
| Cys/2 | 0.2 | 0.4 |
| Val | 6.2 | 6.6 |
| Met | 1.6 | 3.3 |
| Ile | 4.7 | 5.0 |
| Leu | 5.5 | 5.3 |
| Tyr | 4.4 | 4.1 |
| Phe | 4.8 | 4.8 |
| Lys | 3.8 | 3.2 |
| Trp | ND | ND |
| His | 2.6 | 1.8 |
| Arg | 2.2 | 2.3 |

The activity of CGTases according to the present invention is assayed as follows: The mixture of 10 µl enzyme and 0.2% amylose solution in 0.2M buffer is incubated at 50° C. for 10 min. The reaction is stopped by adding 1 ml 0.5M acetic acid and 0.5 ml 0.02% $I_2$/0.2% KI solution. The mixture volume is brought up to 10 ml with distilled water, and extinction is determined under 700 nm. The enzyme activity unit is accepted as the enzyme quantity that has reduced the intensity of blue colour by 10% for 1 min.

The present CGTases acts to the mixture of starch and stevioside, rebaudioside A or the purified Stevia extract to produce alpha-glucosylated stevioside and alpha-glucosylated rebaudioside A.

Starch of various origins, for example, from wheat, corn, potato, tapioca, and sago can be used.

The dextrose equivalent of the partially hydrolyzed starch can be in the range of 5-50, preferably 6-10.

The amount of enzyme to be used for liquefaction of starch is in the limits of 1-5 units/gram of starch, preferably 2-3 units. In the stage of transglycosylation the quantity of enzyme is 7-15 units/gram of starch, preferably 8-11 units. However, the larger the amount of enzyme, the higher the yield of transglycosylated products and the shorter the duration of enzymatic reaction.

The process temperature is 45-70.degree.C., preferably 55-60.degree.C. The reaction rate is increased with increasing reaction temperature. Low temperatures are not favorable.

The following examples illustrate preferred embodiments of the invention.

Experiment 1

Extraction of Sweet Glycosydes

The leaves of *Stevia rebaudiana* are dried at 55.degree.C. for three hour in vacuum oven and powdered (30 mesh). One kg of the obtained material was mixed with 10 liters of water (pH 6.5) and heated to 55.degree.C. with uninterruptedly agitation. 20 grams of PECTINEX Ultra-SP-L is added to the suspension and extraction is carried out at 60.degree.C. for 5 hours. The plant material is separated from the solution by filtration and the pH of the filtrate is adjusted to 10 with calcium hydroxide and heated to 55.degree.C. for 1.0 hours, cooled to ambient temperature with slow agitation, and the resulted residue is removed by filtration.

The pH of resulted filtrate is adjusted to about 7.0 with phosphoric acid, and 220 grams of beta cyclodextrin is added. The solution is maintained at 55.degree.C. for 1.5 hours with agitation, then cooled to about 10.degree.C. for 1 hour, and the formed precipitate is removed by filtration.

The filtrate is collected, mixed with 200 grams of bentonite for water based systems (Sigma-Aldrich), and maintained at 40.degree.C. for one hour. The precipitate is removed by filtration and the resulted clear solution is concentrated at 50-55.degree.C., in vacuum to a syrup state.

In the case for producing the purified extract only without the separation of stevioside and rebaudioside, the solution after bentonite removal is deionized by conventional ion exchange chromatography on Dowex 50WX4-200 ($H^+$) and Amberlite IRA96 ($OH^-$), concentrated and dried. The yield was 116 grams with content of sweet glycosides to about 95%. The mixture contains Dulcoside, 3.2%; Stevioside, 60.4%; Rebaudioside C, 5.7%; and Rebaudioside A, 25.7%.

Experiment 2

Separation and Purification of Rebaudioside A

Fifty grams (on the base of dry material) of the syrup obtained by the process of EXPERIMENT 1 is mixed with 0.25 liters of 96.2% of ethanol and heated to about 50.degree.C. for 30 minutes with slow agitation. The mixture is cooled to the ambient temperature; the resulted precipitate is separated by filtration and dried. The powder weighed 14.2 grams and contained Rebaudioside A, 84.4%; Stevioside, 11.2%; and Rebaudioside C, 4.4%. For the further purification the powder is mixed with five volumes of 95% of ethanol, and treated as in the case of initial syrup. 10.1 grams of rebaudioside A with more than 98% of purity is obtained.

Experiment 3

Separation and Purification of Stevioside

The filtrate obtained in the EXPERIMENT 2 contains Stevioside, 87.7%; rebaudioside A, 0.65%; rebaudioside C, 6.8%; and Dulcoside, 4.8%. of is mixed with 2.0 w/v % of bentonite for organic systems (Sigma-Aldrich) and 2% (w/v) of beta cyclodextrin and heated at 40.degree.C. for about one hour. The suspension is filtered, mixed with equal volume of distilled water, and the ethanol is removed by vacuum evaporation. Deionization of the resulted solution is developed by conventional methods using ion exchange resins, such as Dowex 50WX4-200 (H type) and Amberlite IRA96 (OH type), concentrated and dried. The resulted powder weighed 28.7 grams and contains about 93% of stevioside. For the further purification the powder is mixed with two parts of 90% of ethanol, and at 10-12.degree.C. maintained for about 30 minutes with slow agitation. The precipitate is separated by filtration and dried under vacuum. The product weighed 26.7 grams and contains 98.3% of stevioside.

Experiment 4

Preparation of CGTase of *Thermoactonomyces Vulgaris*

A strain of *Thermoactonomyces vulgaris* INMIA-Tac-3554 was inoculated on 10 liters of a sterilized culture medium (pH 7.0-7.2) containing 1.0% (w/v) soluble starch; 0.5% (w/v) corn steep liquor; 0.5% (w/v) sodium chloride; 0.5% (w/v) peptone; and 0.5% (w/v) calcium carbonate, and the mixture was incubated at a temperature of 50.degree. C. for 20 hours with aeration and stirring. The resultant culture broth was centrifuged and the supernatant was concentrated up to five times on ultrafiltration membranes. The concentrated solution is diluted with three volumes of distilled water and again concentrated to the initial concentrate volume. The process is repeated for three times. A crude enzyme preparation with an activity of about 60,000 units was obtained.

Experiment 5

Preparation of CGTase of *Bacillus Halophilus*

A strain of *Bacillus halophilus* BIO-12H was inoculated on 10 liters of a sterilized culture medium (pH 7.0-7.2) containing 1.0% (w/v) soluble starch; 0.5% (w/v) corn steep liquor; 1.0% (w/v) peptone; 10.0% (w/v) sodium chloride; 2.0% (w/v) potassium chloride; 2.0% (w/v) magnesium sulphate heptahydrate; 1.0% (w/v) manganess sulphate; and 0.5% (w/v) calcium carbonate, and the mixture was incubated at a temperature of 37.degree. C. for 24 hours with aeration and stirring. The resultant culture broth was centrifuged and the supernatant was concentrated up to five times on ultrafiltration membranes. The concentrated solution is diluted with three volumes of distilled water and again concentrated to the initial concentrate volume. The process is repeated for three times. A crude enzyme preparation with an activity of about 40,000 units was obtained.

Experiment 6

Purification of Enzymes

The purification procedure was carried out as follows. Concentrated culture broth (100 ml; 10-11 mg protein per one ml) was mixed with 5 g beta cyclodextrin polymer at 4-5.degree.C. for 16-18 hours. The mixture was centrifuged, and the residue carefully washed in sequence with distilled water, 1M NaCl, and distilled water. The adsorbed enzyme was eluted with 5 mM alpha cyclodextrin in aqueous 0.5 M NaCl at ambient temperature for 3 hours. The eluate was dialyzed against deionized water for 12-14 hours and lyophilized.

At this stage the enzymes from halophilic strain and thermoactinomycete could be purified 53.2- and 57.4-fold, respectively. The degree of the enzyme purification was considerably higher than in the case of adsorption on starch. The method can be used under continuous-flow conditions.

The enzyme solution (10-11 mg lyophilized powder per one ml) was passed through the column (1.6×20 cm) packed and equilibrated with DEAE-β-CD-cellulose copolymer and 0.01 M phosphate buffer (pH 7.0), respectively. The column was washed with 0.5 M NaCl, and the proteins were eluted using a linear gradient of alpha cyclodextrin (from 0 to 10 mM) in 0.01 M phosphate buffer (pH 7.0) containing 0.2 M NaCl. The collected active fractions were dialyzed against 0.01 M phosphate buffer (pH 7.0) containing 1 mM calcium chloride, and the dialyzed fraction was lyophilized.

The yield of enzyme preparations of halophilic strain and thermoactinomycete was about 17% and 15% with the specific activity 76.3 units/mg protein and 95.4 units/mg protein respectively. The protein content was assayed by the Lowry method using serum albumin as a standard protein.

The purity of the enzymes was assayed by gel electrophoresis in 7.5% w/v % polyacrylamide gel, resulting in a single protein band.

The polymer of beta cyclodextrin have been prepared as follows: 55 g of beta cyclodextrin is dissolved in 50 ml of 50% of NaOH solution with the content of 50 mg of $NaBH_4$ at 12-15.degree.C. Then 34 ml of epichlorohydrin is added and the mixture is vigorously stirred at 50.degree.C. for 30-45 min. The resulting gel is suspended in 1000 ml of water with the pH 2-2.5 and boiled with vigorously mixing for 5 min. After that the polymer is separated by filtration, washed with distilled water to pH 6.5-7.0 and dried.

The DEAE polymer of beta cyclodextrin have been prepared as follows: Ten grams of beta cyclodextrin polymer is dried at 80.degree.C. for 14-16 hours and then suspended in the mixture of 50 ml dimethylsulfoxide and 24 g of fine powdered NaOH. After stirring at 60.degree.C. for 1-1.5 hours, 30 g of 2-chlorotriethylamine hydrochloride is added and stirred at room temperature for 30 min. The precipitate is separated by filtration, washed with distilled water until neutral reaction and then dried.

Experiment 7

Enzymatic Treatment of Stevioside, Rebaudioside A and Purified *Stevia* Extract 100 grams of tapioca starch was suspended in 600 ml of distilled water (pH 6.5-7.0), 200 units of crude CGTase obtained in Experiment 4 or 5 was added, and the liquefaction of starch was carried out at 75-80.degree.C. for about one hour to dextrose equivalent about 10. After cooling to 50-60.degree.C., rebaudioside A (obtained in Experiment 2) or stevioside (obtained in Experiment 3) or purified *Stevia* mixture (obtained in Experiment 1) in the amounts of 100 grams was added and mixed until homogeneous solution is obtained. Then, 800 units of crude CGTase were added to the solution, allowed incubation at a temperature of 55.degree. C. for 48 hours, and heated at 100.degree.C. for 10 minutes to inactivate the enzyme. The resulted reaction mixture was decolorized with 1% (w/v) activated carbon, the solution was concentrated at a temperature of 65-70.degree.C. under reduced pressure, and dried.

REFERENCES

Chang, S. S. and Cook, J. M. 1983. Stability studies of stevioside and rebaudioside A in carbonated beverages. J. Agric. Food Chem. 31: 409-412.

Dobberstein, R. H., and Ahmad, M. S. 1982. Extraction, separation and recovery of diterpene glycosides from *Stevia rebaudiana* plants. U.S. Pat. No. 4,361,697.

DuBois, G. E. and Stephenson, R. A. 1984. Diterpenoid sweeteners. Synthesis and sensory evaluation of stevioside analogues with improved organoleptic properties. J. Med. Chem 28:93-98.

Giovanetto, R. H. 1990. Method for the recovery of steviosides from plant raw material. U.S. Pat. No. 4,892,938.

Kitahata, S., Ishikawa, S., Miyata, T. and Tanaka, O. 1989. Production of rubusoside derivatives by transglycosylation of various beta-galactosidase. Agricultural and Biological Chemistry. 53: 2923-2928.

Kutowy, O., Zhang, Q. S., and Kumar, A. 1999. Extraction of sweet compounds from *Stevia rebaudiana* Bertoin. U.S. Pat. No. 5,972,120.

Lobov, S. V., Jasai, R., Ohtani, K., Tanaka, O. and Yamasaki, K. 1991. Enzymatic production of sweet stevioside derivatives: transglycosylation by glucosidases. Agricultural and Biological Chemistry. 55: 2959-2965.

Miyake, T. 1980. Process for producing a sweetener. U.S. Pat. No. 4,219,571.

Morita, T., Fujita, I., and Iwamura, J. 1979. Sweetening compound, method of recovery, and use thereof. U.S. Pat. No. 4,082,858.

Tanaka, O. 1987. Improvement of taste of natural sweetners. Pure Appl. Chem 69:675-683.

Payzant, J. D., Laidler, J. K., and Ippolito, R. M. 1999. Method of extracting selected sweet glycosides from the *Stevia rebaudiana* plant. U.S. Pat. No. 5,962,678.

Phillips, K. C. 1989. *Stevia*: steps in developing a new sweetener. Pages 1-43 in T. H. Grenby ed. Developments in sweeteners, Volume 3. Elsivier Applied Science, London.

Schiffman, S. S., Booth, B. J., Carr, B. T., Losee, M. L., Sattely-Miller, E., and Graham, B. G. 1995. Investigation of synergism in binary mixtures of sweeteners. Brain Res. Bull. 38: 105-120.

Yamamoto, K., Yoshikawa, K. and Okada, S. 1994. Effective production of glucosyl-stevioside by alpha-1,6-transglucosylation of dextran dextranase. Bioscience, Biotechnology, and Biochemistry. 58: 1657-1661.

We claim:

1. A method for producing sweeteners from *Stevia rebaudiana* comprising the following steps:
   a) extracting plant material of *Stevia rebaudiana* with water, in the presence of pectinase, to obtain an aqueous extract;
   b) treating the aqueous extract with beta-cyclodextrin in the amount of 1-5% weight of the aqueous liquid solution, wherein precipitates are formed in the beta cyclodextrin-treated aqueous liquid solution and the formed precipitates are removed from the aqueous liquid solution;
   c) treating the resulting extract from step (b) with bentonite in the amount of 1-5 grams per liter; and
   d) concentrating the resulting extract from step (c) to obtain the sweeteners in the form of a mixture of sweet glycosides.

2. The method according to claim 1, further comprising the following steps:
   e) treating the mixture of sweet glycosides from step (d) with ethanol to obtain a rebaudioside A precipitate;
   f) separating the remaining solution, containing other sweet glycosides, from the rebaudioside A precipitate;
   g) treating the remaining solution with bentonite and beta-cyclodextrin;
   h) desalting the resulting solution from step (g); and
   i) concentrating the resulting solution from step (h) to obtain a stevioside precipitate.

3. The method according to claim 1, further comprising the step of treating the mixture of sweet glycosides from step (d) with cyclodextrin glucanotransferase from *Thermoactinomyces vulgaris* in the presence of carbohydrates to effect transglucosylation of the sweet glycosides.

4. The method according to claim 2, further comprising the step of treating rebaudioside A from step (e) or stevioside from step (i) or both, with cyclodextrin glucanotransferase from *Thermoactinomyces vulgaris* in the presence of carbohydrates to effect transglucosylation of the sweet glycosides.

5. The method according to claim 1, further comprising the step of treating the mixture of sweet glycosides from step (d) with cyclodextrin glucanotransferase from *Bacillus halophilus* in the presence of carbohydrates to effect transglucosylation of the sweet glycosides.

6. The method according to claim 2, further comprising the step of treating rebaudioside A from step (e) or stevioside from step (i) or both, with cyclodextrin glucanotransferase from *Bacillus halophilus* in the presence of carbohydrates to effect transglucosylation of the sweet glycosides.

7. A process for recovering sweet glycosides from *Stevia rebaudiana* plant material, which comprises the following steps:

a) treating the *Stevia rebaudiana* plant material with hot water to form a suspension so as to extract mixed sweet glycosides from the *Stevia rebaudiana* plant, wherein during the extraction the suspension is treated with pectinase;

b) separating the *Stevia rebaudiana* plant material in the suspension from the water to obtain an aqueous liquid solution containing the mixed sweet glycosides;

c) adding into the aqueous liquid solution from step (b) beta cyclodextrin in the amount of 1-5% weight of the aqueous liquid solution, wherein precipitates are formed in the beta cyclodextrin-treated aqueous liquid solution and the formed precipitates are removed from the aqueous liquid solution;

d) adding into the aqueous liquid solution from step (c) bentonite in the amount of 1-5 grams per liter, wherein the bentonite-treated aqueous liquid solution is filtered to produce a filtrate; and e) evaporating the filtrate from step (d) to syrup state or dryness.

8. The process according to claim 7, wherein the beta cyclodextrin added is preferably in the amount of 2.0-2.5% weight of the aqueous liquid solution, and the bentonite added is preferably in the amount of 2-3 grams per liter.

9. A process for the purification of rebaudioside A and stevioside, which comprises the following steps:

a) dissolving the mixture of sweet glycosides obtained in step (e) of claim 7 with ethanol-water solution, heating the solution and then cooling the solution to precipitate Rebaudioside A;

b) filtering the solution to recover crystalline Rebaudioside A and a filtrate containing other sweet glycosides;

c) suspending the crystalline Rebaudioside A obtained in step (b) in ethanol-water solution, heating and then cooling the solution to precipitate the Rebaudioside A at a higher purity;

d) recovering the higher purity Rebaudioside A;

e) treating the filtrate obtained in step (b) with bentoninte;

f) treating the filtrate obtained in step (e) with beta cyclodextrin;

g) desalting and concentrating the filtrate from step (f) by heating and evaporating to dryness to obtain crystalline Stevioside;

h) suspending the crystalline stevioside obtained in step (g) in ethanol, heating and then cooling the solution to precipitate the Stevioside at a higher purity; and i) recovering the higher purity Stevioside.

10. The method according to claim 1, wherein the beta cyclodextrin added is preferably in the amount of 2.0-2.5% weight of the aqueous liquid solution, and the bentonite added is preferably in the amount of 2-3 grams per liter.

\* \* \* \* \*